United States Patent [19]

Corey

[11] Patent Number: 4,668,822

[45] Date of Patent: May 26, 1987

[54] METHOD FOR PREPARING (+)S-2-HYDROXY-2-METHYL-HEXANOIC ACID

[75] Inventor: Paul F. Corey, Elkhart, Ind.

[73] Assignee: Miles Laboratories, Inc., Elkhart, Ind.

[21] Appl. No.: 894,390

[22] Filed: Aug. 11, 1986

Related U.S. Application Data

[63] Continuation of Ser. No. 723,201, Apr. 15, 1985.

[51] Int. Cl.$^4$ .............................................. C07C 59/01
[52] U.S. Cl. .................................... 562/579; 544/105
[58] Field of Search ......................................... 562/579

[56] References Cited

FOREIGN PATENT DOCUMENTS 53-108922  9/1978  Japan ................................... 562/579

OTHER PUBLICATIONS

Terashima et al. I, *Chemistry Letters*, pp. 1109–1112, (1977).
Terashima et al. II, *Tetrahedron Letters*, No. 11, pp. 1005–1008, (1977).
Jew et al. I, *Tetrahedron*, vol. 35, pp. 2337–2343, (1979).
Jew et al. II, *Tetrahedron*, vol. 35, pp. 2345–2352 (1979).
Koga et al., *Chemical Abstracts*, vol. 90, No. 121225u, (1979).
Marshalok et al., *Chemical Abstracts*, vol. 95, No. 61428d, (1981).

*Primary Examiner*—Natalie Trousof
*Assistant Examiner*—Bruce D. Gray
*Attorney, Agent, or Firm*—Edward P. Gray

[57] ABSTRACT

A method for preparing an important stereo-specific intermediate in the synthesis of prostaglandin analogs is disclosed. Said intermediate is (+)S-2-hydroxy-2-methyl-hexanoic acid and is prepared via an asymmetric halolactonization reaction utilizing L-proline as the chiral agent.

3 Claims, No Drawings

METHOD FOR PREPARING (+)S-2-HYDROXY-2-METHYL-HEXANOIC ACID

This is a continuation of application Ser. No. 723,201 filed Apr. 15, 1985, now pending.

The prostaglandins as a class have been the focus of intense investigation in recent years. Being derivatives of prostanoic acid, either naturally occurring or synthetic prostaglandins possess the ability to elicit a wide range of biochemical and physiological effects including cardiovascular, nervous, reproductive, renal and gastric system responses in animals. These responses may be brought about by the administration of doses as small as about 10 ng/kg of body weight of one or more of such prostaglandins. Early isolation of these highly active compounds was achieved principally by extraction from mammalian tissues. However, such extraction processes are typically not commercially feasible nor do they provide sufficient quantities for adequate pharmacological evaluation. Synthetic methods have advanced to where sufficient quantities may be produced through complete chemical synthesis; however, this methodology suffers from the disadvantage of being essentially nonstereospecific hence leading to tedious resolution procedures which must be carried out to obtain the desired optically active isomer. It is well-known in the art that the most active prostaglandin derivatives have specific stereochemical configurations at each asymmetric carbon atom and/or double bond.

16-methyl-1,11α,16RS-trihydroxyprost-13E-en-9-one (hereinafter referred to as TR-4698) is a prostaglandin analog which is disclosed and claimed in U.S. Pat. No. 4,132,738 issued Jan. 2, 1979 to Kluender, et al which is, as well as all other references cited herein, incorporated by reference. TR-4698 is a mixture of two isomers at the chiral C-16 position. The 16-S isomer (i.e., 16-methyl-1, 11α,16S-trihydroxy-prost-13E-en-9-one, hereinafter referred to as TR-7134) is believed to possess superior physiological activity to that of the 16-R isomer (hereinafter referred to as TR-7133). Hence, it has become desirable to design the synthesis of an intermediate having the requisite stereochemistry, which when ultimately incorporated into the molecule, would provide the 16-S isomer only (TR-7134) rather than the racemic mixture. Such an intermediate is (+)S-2-hydroxy-2-methyl-hexanoic acid which may be prepared (as described subsequently) via an asymetric halolactonization reaction utilizing L-proline as the chiral agent. This intermediate may then be incorporated into the synthesis of TR-7134 as reviewed hereinafter.

DESCRIPTION OF PERTINENT ART

Various techniques have been utilized in the preparation or isolation of physiologically active prostaglandin isomers. One such technique is to utilize a resolved intermediate possessing the appropriate stereochemistry at the chiral center for incorporation into the molecule. For example, Pappo, et al in "Chemistry, Biochemistry and Pharmacological Activity of Prostanoids", edited by S. M. Roberts and F. Scheinmann, Pages 17-26, Pergammon Press, N.Y., 1978, teach the resolution of racemic 2-hydroxy-2-methyl-hexanoic acid via its naphthylethylamine salt for preparation of a chiral acetylenic alcohol. (This optically active acetylenic alcohol may then be incorporated as the "right-hand" portion of the prostaglandin analog by following known techniques). However, the classical resolution of the racemic 2-hydroxy-2-methyl-hexanoic acid is tedious at best and requires an expensive, optically active amine.

Another approach taught by Y. Fujimoto, J. Yadev, and C. Sih in Tetrahedron Letters, 21, 1481 (1980) prepares (—)S-2-methyl-hexane-1,2-diol from (+)citramalic acid, the chiral diol then being used to prepare the corresponding optically active acetylenic alcohol. The disadvantage of this method is that the citramalic acid must be prepared from mesaconic acid using an isolated microbial enzyme.

S-s. Jew, S. Terashima and K. Koga in Tetrahedron, 35, 2337, et seq (1970), and papers cited therein, teach the use of an asymmetric halolactonization reaction to prepare optically active α,α-disubstituted-α-hydroxy acids from α,β-unsaturated acids. However, the technique described therein suffers from the disadvantage of being unable to render the S-isomer of the resulting α-α-disubstituted-α-hydroxy acid in high optical purity. For example, Jew, et al teach that when trans-2-methyl-2-butenoic acid is utilized as the starting compound, the R-isomer of the resulting 2-hydroxy-2-methyl butanoic acid is formed in high predominance to the S-isomer (approximately 95:5, respectively). Similarly, when cis-2-methyl-2-butenoic acid was investigated as the starting material, the R-isomer of the resulting 2-hydroxy-2-methyl butanoic acid was still predominant although a shift toward the S-isomer was observed (approximately 60:40, respectively). Hence, a need still exists for a method of preparing the S-isomer of such α,α-disubstituted-α-hydroxy acids in high optical purity.

The invention described herein teaches such a method for preparing (+)S-2-hydroxy-2-methyl-hexanoic acid which may be used as described subsequently in the preparation of certain optically active prostaglandin analogs such as TR-7134. The method of the present invention prepares (+)S-2-hydroxy-2-methyl-hexanoic acid by utilizing a technique similar to that described by Jew et al, supra. However, rather than using an α,β-unsaturated acid as the starting material as taught by Jew et al, it has been found that 2-methylene hexanoic acid can be used as described hereinafter to prepare (+)S-2-hydroxy-2-methyl-hexanoic acid of high optical purity.

SUMMARY OF THE INVENTION

The present invention is directed to a method for preparing the stereospecific prostaglandin intermediate (+)S-2-hydroxy-2-methyl-hexanoic acid. Said method is accomplished by reacting 2-methylenehexanoyl chloride with L-proline in the presence of a base to form an amide of the formula:

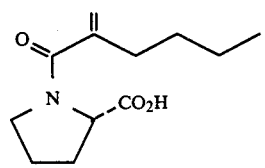

This amide is then reacted with N-bromosuccinimide in an aprotic polar solvent forming a bromolactone of the formula:

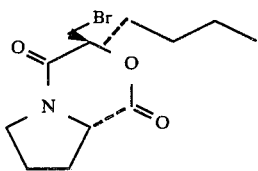

Dehalogenation of said bromolactone is then achieved with tri-n-butyltin hydride in methylene chloride to form the following oxazine:

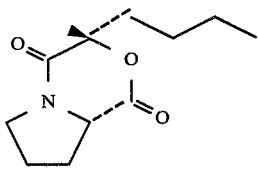

This oxazine is then hydrolyzed with concentrated hydrobromic acid thereby effecting formation of (+)S-2-hydroxy-2-methyl-hexanoic acid, a valuable intermediate used in the preparation of prostaglandin analogs.

DETAILED DESCRIPTION OF THE INVENTION

The method of the present invention provides for the preparation of (+)S-2-hydroxy-2-methyl-hexanoic acid via an asymmetric halolactonization reaction utilizing L-proline as the chiral agent. The reaction scheme for the preparation of (+)S-2-hydroxy-2-methyl-hexanoic acid is depicted in Table 1.

2-methylene hexanoic acid is first converted to the respective acid chloride (step A) by the method of Ikakura, Sato and Matsuo, *Nippon Kagaku Zasshi*, 80, 502 (59); CA 55: 3427 g. Said acid chloride is then added to an approximately equivalent amount of L-proline in a mixture of $H_2O$ and diethyl ether (step B). The pH of the resulting mixture is maintained at about 10-11 by the addition of concentrated aqueous NaOH. The mixture is stirred at ambient temperature for about 15 minutes to about 2 hours followed by isolation of the resultant amide utilizing conventional extraction techniques. Bromolactonization is then effected (step C) by adding N-bromosuccinimide (NBS) to a solution of said amide in an aprotic polar solvent such as dimethylformamide (DMF) or dimethylsulfoxide (DMSO). The resulting mixture is then stirred at ambient temperature for about 12 to about 36 hours to yield the bromolactone which is then isolated by conventional techniques such as described hereinafter. The bromolactone is then dehalogenated to the corresponding oxazine (step D) by heating a mixture of said bromolactone, tri-n-butyltin hydride, and benzoyl peroxide in methylene chloride at reflux temperature for about 15 to about 36 hours. The oxazine is then readily hydrolyzed (step E) to (+)S-2-hydroxy-2-methylhexanoic acid by, for example, heating said oxazine at about 100°-105° C. in the presence of concentrated HBr for a time sufficient to effect said hydrolysis (typically from about 15 to about 24 hours).

The (+)S-2-hydroxy-2-methyl-hexanoic acid prepared by the method of this invention may then be utilized (by following known techniques) in the formation of certain stereospecific prostaglandin analogs, described briefly as follows. Utilizing the procedure of Pappo, et al, cited supra, the (+)S-2-hydroxy-2-methylhexanoic acid can be used to prepare the corresponding stereospecific acetylenic alcohol, i.e., 4-methyloct-1-yn-4S-ol. See the reaction sequence shown in Table 2.

TABLE 2

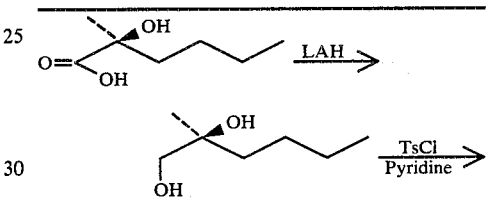

TABLE 1

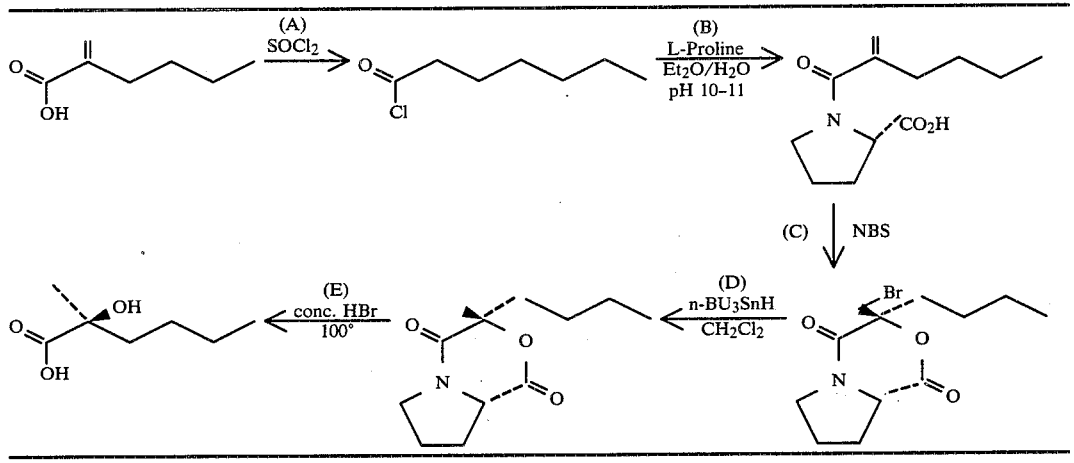

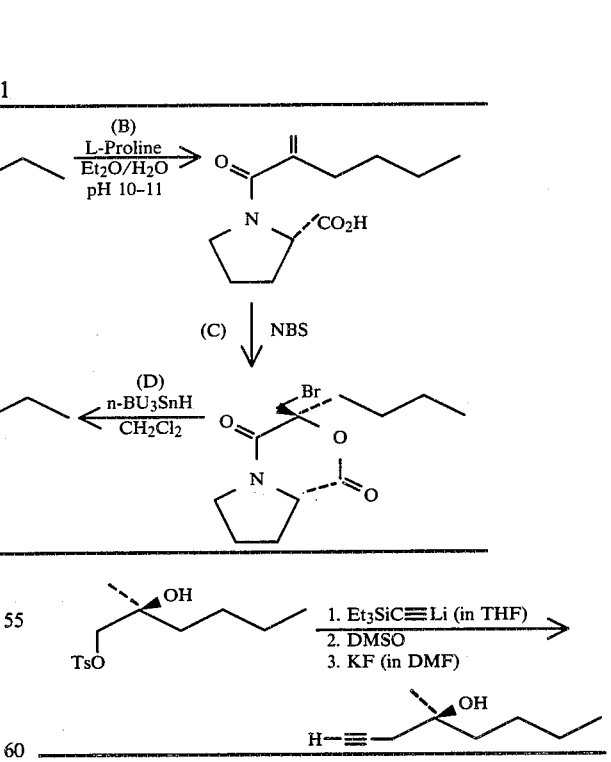

As depicted in Table 2, (+)S-2-hydroxy-2-methylhexanoic acid is reduced with lithium aluminum hydride to yield the corresponding diol which is subsequently treated with tosyl chloride in pyridine to form the monotosylate. A three equivalent excess of lithium triethylsilylacetylide (formed in situ) is added to the monotosylate forming an intermediate epoxide which is opened upon treatment with dimethyl sulfoxide. Purification after work-up with potassium fluoride in dimethylformamide renders the desired stereospecific acetylenic alcohol, 4-methyloct-1-yn-4S-ol.

As taught by Kluender et al, (U.S. Pat. No. 4,132,738, cited supra the above acetylenic alcohol is then converted to the corresponding iodovinyl alcohol. The hydroxyl function of the iodovinyl alcohol is protected with an acid-labile hydroxy protecting group (or alternatively, the hydroxyl group of the acetylenic alcohol can be protected prior to conversion of the alcohol to the iodovinyl compound). The hydroxy-protected iodovinyl alcohol is then lithiated with t-butyllithium and reacted with a solubilized ligand complex of a copper (I) compound such as (hexamethylphosphoroustriamide)$_2$-copper (I) pentyne to yield the corresponding organolithiocuprate. This organolithiocuprate is then reacted with 4R-(tetrahydropyran-2-yloxy)-2-[7-tetrahydropyran-2-yloxy)heptyl]-2-cyclopent-2-enone to form the tetrahydropyran-protected form of TR-7134. Said protected form is then hydrolyzed with a weak acid to render TR-7134. Clearly, one skilled in the art will appreciate that other prostaglandin analogs may be prepared using the optically active (+)S-2-hydroxy-2-methyl-hexanoic acid by the procedure described above or other techniques known to the art.

The following examples are set forth as a means of illustrating the present invention and are not to be construed as a limitation thereon.

EXAMPLE 1

Preparation of (+)S-2-hydroxy-2-methyl-hexanoic acid (a) N-(2-Methylene-hexanoyl)-L-proline A stirred mixture of 31.5 grams (g) of L-proline, 111.0 g of NaHCO$_3$, 510 milliliters (ml) H$_2$O and 210 ml of diethyl ether was maintained in an ambient temperature bath at pH 10.5-10.7 (adjusted by the addition of concentrated aqueous NaOH). To this mixture was added a solution of 44 g of 2-methylenehexanoyl chloride (prepared by the method of Ikakura et al, supra) in diethyl ether (60 ml) in portions over about 20 minutes while maintaining the pH at 10.5-10.7 after which the mixture was stirred for about 0.5 hour at ambient temperature. The resulting immiscible phases were then separated, and the aqueous phase was extracted with two 200 ml portions of diethyl ether which were combined and then washed with two 100 ml portions of H$_2$O. The aqueous extracts were added to the aqueous phase which was then acidified to pH 1 with concentrated aqueous HCl and then extracted with four 200 ml portions of ethyl acetate. The combined ethyl acetate extracts were washed with about 100 ml of brine (saturated aqueous sodium chloride solution) and then dried over MgSO$_4$. The resulting solution was filtered and evaporated in vacuo to render 62.4 g of the title compound (of Example 1a) as a pale yellow viscous syrup having the following spectral characteristics:

ir (CHCl$_3$) 2950, 1720, 1610, 1445, 1210, 910 cm$^{-1}$; nmr (CDCl$_3$) δ 9.68 (br, s, 1H), 5.30 (S, 1H), 5.24 (S, 1H), 4.63 (t, J=7, 1H), 3.63 (t, J=6, 2H), 1.70-2.50 (m, 6H), 1.10-1.70 (m, 4H), 0.91 (t, J=7, 3H); C$^{13}$ nmr (CDCl$_3$) ppm 174.3, 172.2, 145.3, 115.95, 59.2, 49.6, 33.4, 29.7, 28.5, 25.0, 22.4, 13.8; R$_f$ (System II)=0.308 ("System II" is defined as the organic layer from a mixture of ethyl acetate, acetic acid, isooctane, and water in a ratio of 11:2:5:10, respectively).

(b) 3S-Bromomethyl-3-n-butyl-1,4-dioxo-3,4,6,7,8,8α S-hexahydro-1H-pyrrolo[2,1-c]-[1,4]oxazine A solution of N-(2-methylene-hexanoyl)-L-proline (39.3 g) in 575 ml of dry dimethylformamide was maintained at ambient temperature protected from light under an inert gas atmosphere. To this was added 62.0 g of N-bromosuccinimide and the resulting solution was stirred for 20 hours after which it was poured into a mixture of saturated aqueous NaHCO$_3$ (2.5 liters) and ethyl acetate (700 ml) and shaken vigorously. The phases were separated and the aqueous phase was extracted with three 500 ml portions of ethyl acetate. The ethyl acetate extracts were combined and then washed with five 250 ml portions of H$_2$O. The H$_2$O extracts were combined and then back-washed with ethyl acetate. The combined ethyl acetate extracts were washed with four 175 ml portions of saturated aqueous Na$_2$S$_2$O$_3$. The combined aqueous Na$_2$S$_2$O$_3$ extracts were back-washed with 100 ml of ethyl acetate and all ethyl acetate extracts were combined and washed with two 250 ml portions of brine and then dried (MgSO$_4$). The resulting solution was filtered and the filtrate was evaporated in vacuo to yield a brown syrup which was subsequently taken up in a minimal amount of ethyl acetate and pushed through a 1.5"×4" silica gel dry column with ethyl acetate. The eluant (about the first 250 ml) was collected and evaporated in vacuo to give 49.6 g of residue which was crystallized from diethyl ether (50 ml) to give about 22 g of the title compound (of Example 1b) as white needles. The mother liquor from the crystallization was freed of solvent and chromatographed on silica using a 7.5% diethyl ether in CH$_2$Cl$_2$ solvent. The major band (R$_f$=0.35; 7.5% Et$_2$O in CH$_2$Cl$_2$) was isolated, evaporated in vacuo and crystallized from diethyl ether to give an additional 10.85 g of the title compound. Two recrystallizations from diethyl ether gave the analytical sample as rods or square prisms, melting point (m.p.) 73.5°-74.5° C. The material had the following spectral characteristics:

ir (CHCl$_3$) 2950, 1752, 1665, 1460, 1355 cm$^{-1}$; nmr (CDCl$_3$) δ 4.40-4.70 (m, 1H), 3.87 (d, |J$_{AB}$|=11.1, 1H) and 3.59 (d, |J$_{AB}$|=11.1, 1H) [center of pattern: 3.73, αv$_{AB}$=24.59 H$_z$], 3.50-3.90 (m, 2H), 2.40-2.70 (m, 1H), 1.70-2.30 (m, 5H), 1.10-1.50 (m, 4H), 0.89 (t, J=6, 3H); C$^{13}$ nmr (CDCl$_3$) ppm 166.4, 163.7, 88.7, 58.0, 45.1, 38.1, 37.7, 30.0, 25.9, 22.4, 21.6, 13.7; [α]$_D$=−134.29 (C=2.0835 in CHCl$_3$).

Elemental analysis for C$_{12}$H$_{18}$BrNO$_3$: Calculated: C, 47.38; H, 5.96; N, 4.61. Found: C, 47.55; H, 6.21; N, 4.62.

(c) 3S-Methyl-3-n-butyl-1,4-dioxo-3,4,6,7,8,8-αS-hexahydro-1H-pyrrolo-[2,1-c][1,4]oxazine A solution of 25.8 g of the title compound of Example 1(b) in 700 ml of methylene chloride (prepared and purified by passage through an alumina column) was treated (at ambient temperature) with tri-n-butyltin hydride (35 ml) and benzoyl peroxide (140 mg) and the resulting mixture was then heated at reflux temperature for about 18 hours with simultaneous light irradiation. The mixture was then cooled and the solvent was evaporated under reduced pressure to give 69.9 g of a residue which was chromatographed on a 2"×19.5" silica gel column eluted with 7.5% diethyl ether in methylene chloride. The major product band (R$_f$=0.25; 7.5% Et$_2$O in CH$_2$Cl$_2$) was isolated and the solvent removed by evaporation in vacuo. The crude product was subsequently crystallized from 60 ml of a mixture of diethyl ether/hexane (1:3) to give 16.42 g of the title compound (of Example 1c), as a fine white wool, m.p. 68°–69.5° C. The material had the following spectral characteristics:

ir (CHCl$_3$) 2945, 1745, 1665, 1460, 1352, 1045 cm$^{-1}$; nmr (CDCl$_3$) δ 4.15–4.40 (m, 1H), 3.50–3.80 (m, 2H), 1.65–2.70 (m, 6H), 1.57 (s, 3H), 1.10–1.50 (m, 4H), 0.90 (t, J=6, 3H); C$^{13}$ nmr (CDCl$_3$) ppm 168.2, 166.9, 86.5, 57.5, 45.4, 37.8, 29.8, 25.6, 24.1, 22.8, 22.3, 13.9; [α]$_D$=−160.35 (C=1.2645 in CHCl$_3$).

Elemental analysis for C$_{12}$H$_{19}$NO$_3$: Calculated: C, 63.97; H. 8.50; N, 6.22. Found: C, 64.03; H, 8.55; N, 6.42.

(d) (+)S-2-hydroxy-2-methyl-hexanoic acid

A mixture of 14.75 g of the title compound of Example 1(c) in 200 ml of 48% aqueous HBr was prepared and heated to about 100°–105° C. for 19.5 hours and then cooled. The mixture was then poured into 1 liter of brine and was extracted with two 500 ml portions of CH$_2$Cl$_2$. The CH$_2$Cl$_2$ layers were then combined and washed with 400 ml of H$_2$O (discarding the H$_2$O washings), concentrated in vacuo to about 100 ml and then exhaustively extracted with saturated aqueous NaHCO$_3$. The NaHCO$_3$ extracts were combined and acidified to pH 1 with concentrated aqueous HCl and subsequently extracted with five 100 ml portions of ethyl acetate. The ethyl acetate extracts were combined and washed with several portions of brine (until the pH was about 4) and then dried over MgSO$_4$, filtered and the filtrate was evaporated to dryness to give 6.4 g of (+)S-2-hydroxy-2-methyl-hexanoic acid. This material was recrystallized twice from a mixture of diethyl ether/hexane (1:10) to render the title compound having the following characteristics: m.p.=70.5°–72° C.; ir (CHCl$_3$) 2950, 1710, 1462, 1272, 1170, 1060 cm$^{-1}$; nmr (CDCl$_3$) δ 6.84 (v.br.s, 2H), 1.50–1.90 (m, 2H), 1.47 (s, 3H), 1.10–1.50 (m, 4H), 0.90 (t, J=6, 3H); C$^{13}$ nmr (CDCl$_3$) ppm 181.7, 74.9, 39.9, 25.9, 25.8, 22.8, 13.9; [α]$_{365}$=+24.05 (C=1.537 in H$_2$O (Lit., Pappo et al, supra: [α]$_{365}$=+23.4 (H$_2$O).

While the present invention has described in detail a method for preparing (+)S-2-hydroxy-2-methyl-hexanoic acid it is to be recognized that analagous procedures can be used to prepare other like-substituted alkanoic acids. Accordingly, such procedures are deemed to be comtemplated equivalents to the claimed method of the present invention.

What is claimed is:

1. A method for preparing (+)S-2-hydroxy-2-methyl-hexanoic acid of high optical purity comprising:

(a) reacting 2-methylene-hexanoyl chloride with L-proline in the presence of a base forming an amide of the formula:

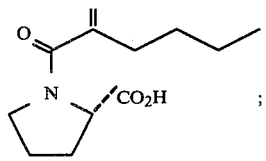

(b) reacting said amide with N-bromosuccinimide in an aprotic polar solvent forming a bromolactone of the formula:

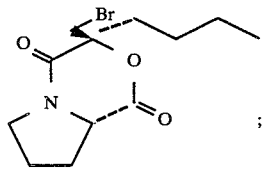

(c) dehalogenating said bromolactone with tri-n-butyltin hydride in methylene chloride forming an oxazine of the formula:

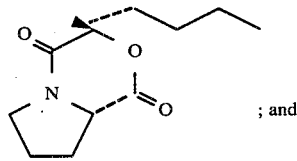

; and (d) hydrolyzing said oxazine with concentrated hydrobromic acid to effect formation of (+)S-2-hydroxy-2-methyl-hexanoic acid.

2. The method of claim 1 wherein the base according to step (a) thereof is sodium hydroxide.

3. The method of claim 1 wherein the aprotic polar solvent according to step (b) thereof is dimethylformamide.

* * * * *